US 6,691,363 B2

(12) United States Patent
Huen

(10) Patent No.: US 6,691,363 B2
(45) Date of Patent: Feb. 17, 2004

(54) POWER-DRIVEN TOOTHBRUSH

(75) Inventor: Raico Huen, San Po Kong (HK)

(73) Assignee: Oasis Global Limited, Tortola (VG)

( * ) Notice: Subject to any disclaimer, the term of this patent is extended or adjusted under 35 U.S.C. 154(b) by 96 days.

(21) Appl. No.: 10/047,491

(22) Filed: Oct. 26, 2001

(65) Prior Publication Data

US 2002/0100129 A1 Aug. 1, 2002

(30) Foreign Application Priority Data

Oct. 26, 2000 (CN) ......................................... 00262662 U

(51) Int. Cl.⁷ .............................. A46B 13/02; A46B 7/06
(52) U.S. Cl. ........................................................ 15/22.1
(58) Field of Search ............................ 15/22.1, 23, 28, 15/22.2

(56) References Cited

U.S. PATENT DOCUMENTS

| 2,044,863 A | * | 6/1936 | Sticht |
| 3,201,670 A | * | 8/1965 | Myers |
| 3,382,519 A | * | 5/1968 | Piggott |
| 4,277,861 A | * | 7/1981 | Lex |
| 5,000,684 A | * | 3/1991 | Odrich |

* cited by examiner

*Primary Examiner*—Randall E. Chin
(74) *Attorney, Agent, or Firm*—Kenyon & Kenyon

(57) ABSTRACT

A power-driven toothbrush comprising a brush head 1 mounted on a brush handle 2 for vibratory movement relative thereto, a vibration transmitting arm 33 extending between said handle 2 and said head 1 and a vibration actuator 3 located within the handle 2, said vibration transmitting arm 33 including a magnet 34 located within said handle 2 and the actuator 2 including a solenoid 32 adjacent said magnet 34 and means for supplying AC current to the solenoid 32 a frequency which is the same as the resonant frequency of the vibration transmitting arm 33. The means for supplying AC current to said solenoid includes a printed circuit board 31. The frequency of the AC current delivered to the solenoid and the natural frequency of the vibration transmitting arm are in the range of 100–300 Hz.

5 Claims, 3 Drawing Sheets

POWER-DRIVEN TOOTHBRUSH

FIELD OF INVENTION

This invention relates to power-driven toothbrushes.

BACKGROUND TO THE INVENTION

Conventional power-driven toothbrushes are usually driven by electric motors. The size of the motor determines the frequency of vibration of such toothbrushes. A large enough motor must be used to achieve a high enough frequency of vibration to clean teeth quickly and effectively. Such motors expend significant amounts of energy. As a result these toothbrushes are bulky and heavy, the battery lifetime is short and the service life of the toothbrush is reduced.

STATEMENT OF INVENTION

According to the present invention there is provided a power-driven toothbrush comprising a brush head mounted on a brush handle for vibratory movement relative thereto, a vibration transmitting arm extending between said handle and said head and a vibration actuator located within the handle, said vibration transmitting arm including a magnet located within the handle and the actuator including a solenoid adjacent said magnet and means for supplying AC current to the solenoid at a frequency which is the same as the resonant frequency of the vibration transmitting arm.

Accordingly, the present invention provides a power-driven toothbrush having a brush which vibrates at a high enough frequency to clean teeth quickly and effectively by causing the vibration transmitting arm to vibrate at its resonant frequency, thereby minimizing power consumption and extending the service life of the toothbrush.

Preferably, the means for supplying AC current to said solenoid includes a printed circuit board.

Preferably, the frequency of the AC current delivered to the solenoid and the natural frequency of the vibration transmitting arm are in the range of 100–300 Hz Preferably the means for supplying AC current include an internal or external power supply providing AC current. Alternatively, the means for supplying AC current include an internal or external power supply providing DC current, which is converted to AC current by the printed circuit board.

BRIEF DESCRIPTION OF THE DRAWINGS

An embodiment of the present invention is illustrated in the accompanying drawings by way of example only, in which.

DETAILED DESCRIPTION OF THE INVENTION

Figure 1:
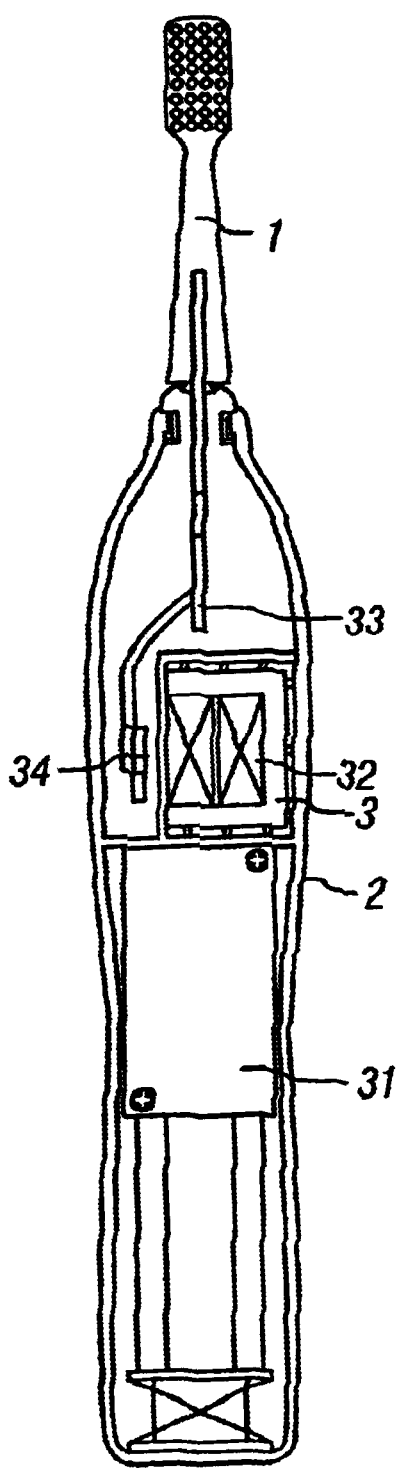
FIG. 1 is a rear view of a side-section of the power-driven toothbrush.
Figure 2:
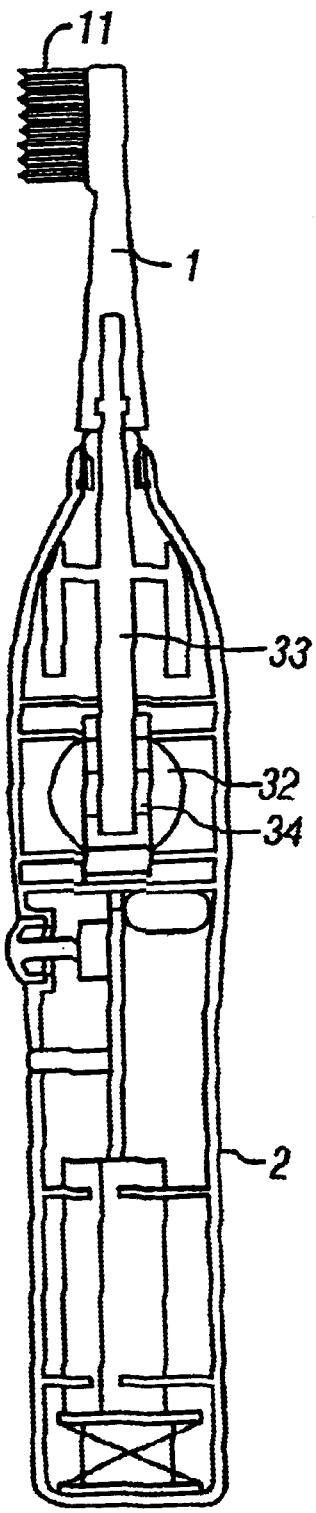
FIG. 2 is a side view of a side-section of the power-driven toothbrush show in FIG. 1.

Referring to FIGS. 1 and 2 of the accompanying drawings, an embodiment of a power-driven toothbrush of the present invention comprises a brush head 1, brush handle 2, vibration transmitting arm 33, a vibration actuating device 3 installed within the brush handle 2 and means for supplying AC current to the vibration actuating device (not shown).

Figure 3:
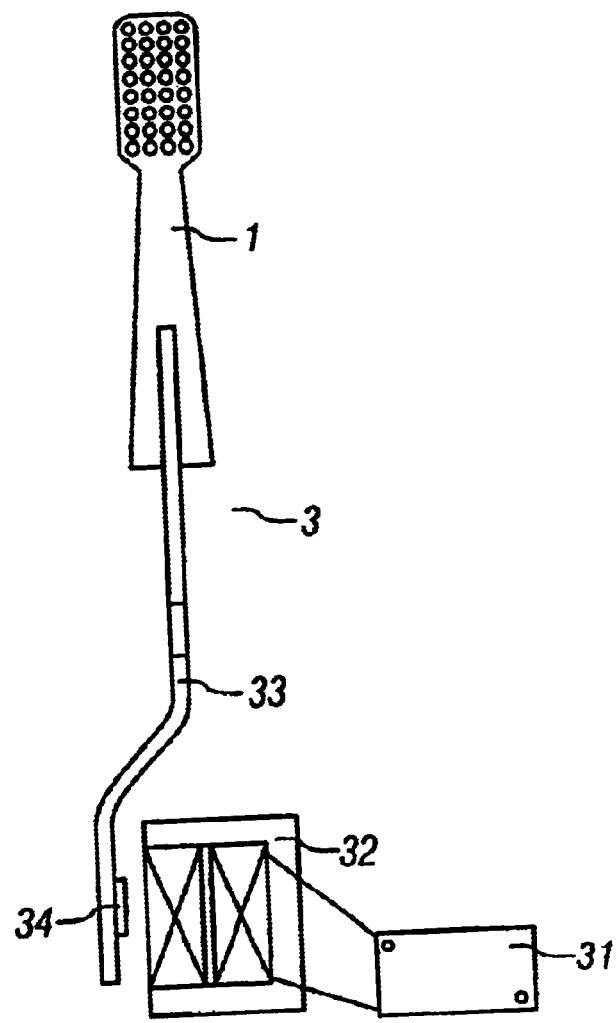
FIG. 3 is a schematic view of the brush head and actuating means of the toothbrush shown in FIG. 1.

The vibration actuating device 3 depicted in FIG. 3 comprises a solenoid 32. The solenoid 32 is connected to a printed circuit board (PCB) 31 which is in turn electrically connected to an power supply (not shown). The power supply may be provided internally or externally to the toothbrush. As a result the PCB 31 delivers an AC current to solenoid 32. In the present invention the AC current supplied to the solenoid 32 has a frequency in the range of 100 Hz to 300 Hz. The vibration transmitting arm 33 extends from the brush head 1 towards the solenoid 32 within the handle 2. A magnet 34 is connected to the vibration transmitting arm 33 and arranged so that it is disposed face to face to the solenoid 32.

Figure 5:
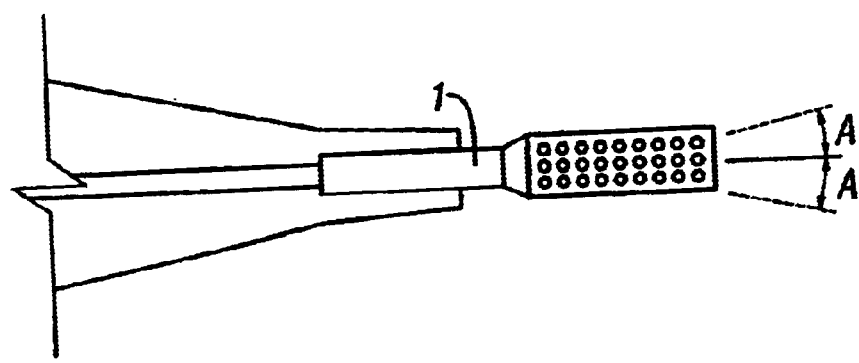
FIG. 5 is a perspective view from above of the brush head of the toothbrush in FIG. 1 showing the amplitude at resonance.
Figure 4A:
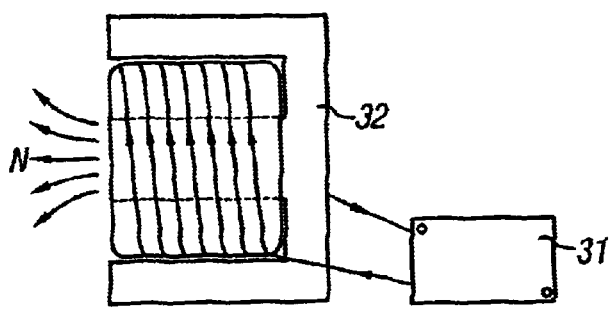
FIGS. 4A and 4B are schematic views of the solenoid of the toothbrush as shown in FIG. 1 with different polarities due to the effects of the AC current.
Figure 4B:
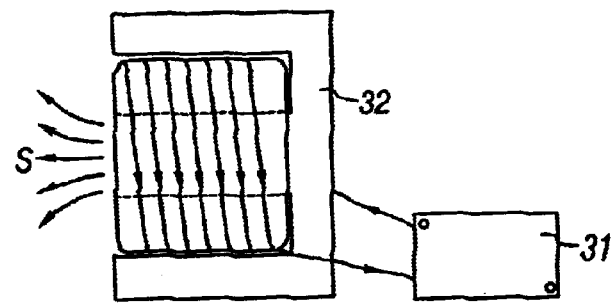

The working principle of solenoid 32 is shown in FIGS. 4A and 4B. Electric current from the power supply (not shown), after being regulated by PCB 31, is delivered to the solenoid in the form of AC current with a frequency of between 100 Hz to 300 Hz. The magnetic polarity of the solenoid 32 chances due to the alternating phase of the AC current. The frequency of the change in polarity matches that of the frequency of the AC current supplied to the solenoid. FIG. 4A shows the left-hand side of solenoid 32 having a north pole and 4B shows the left-hand side of solenoid 32 having a south pole when the current is directed in the opposite phase to 4A. The magnet 34 disposed face to face to the left-hand side of the solenoid 32 is attracted and repelled as the polarity of the solenoid 32 changes. As a result the vibration transmitting arm 33 and consequently the brush head 1 vibrates as shown in FIG. 5. When the frequency of the power supplied to the solenoid matches the natural frequency of the vibration transmitting arm 33 the arm resonates and the amplitude of vibration reaches a maximum value. In the present invention the amplitude of vibration varies between 0.5 and 2.0 mm.

It is understood that the power supply of the present invention may supply AC or DC current to the PCB 31. If DC current is supplied then it is converted by the PCB 31 so that an alternating current is always delivered to the solenoid.

Figure 6:
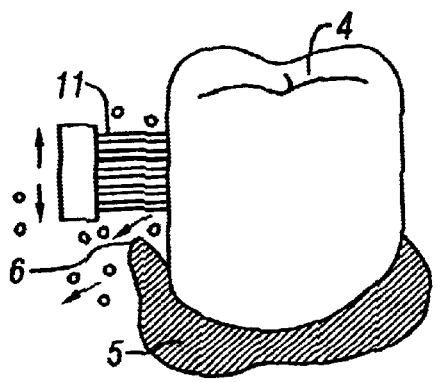
FIGS. 6, 7 and 8 are side and perspective views showing the toothbrush of FIG. 1 in use.
Figure 7:
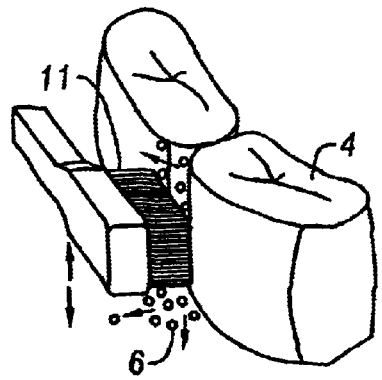
Figure 8:
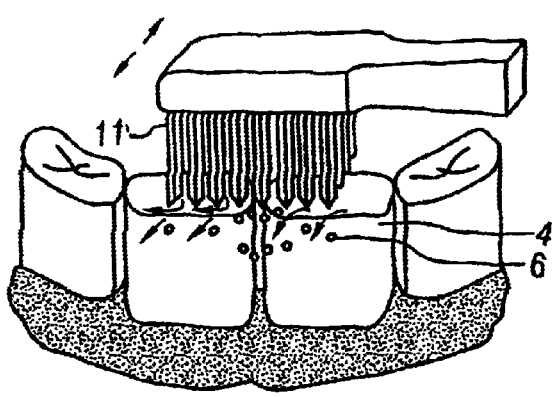

FIGS. 6, 7 and 8 illustrate the toothbrush of the present invention in use. As the toothbrush resonates the brush hair 11 moves liquid, such as toothpaste and saliva, between the teeth 4 and also in the region between the teeth 4 and gum 5. The vibration of the resonating toothbrush against the teeth has an effect similar to a sound wave. As a result of the vibrating notion of the toothbrush bacteria 6 is dislodged from these regions and brushed away. The teeth are quickly and effectively cleaned. However, the amount of energy utilized to achieve this effect is a minimum since the toothbrush is resonating at its natural frequency.

It should be appreciated that that above described power driven toothbrush represents a preferred embodiment of the present invention. Various modifications may be made to this embodiment without departing from the scope of the present invention.

What is claimed is:

1. A power-driven toothbrush comprising a brush head mounted on a brush handle for vibratory movement relative thereto, a vibration transmission arm extending between said handle and said head, the arm having a longitudinal extent and having a predetermined frequency of resonance in a vibrational mode orthogonal to its longitudinal extent, and a vibration actuator located within the handle, said vibration transmitting arm including a magnet located within said handle and the actuator including a solenoid adjacent said magnet and means for supplying AC current to the solenoid at a frequency which is the same as the frequency of resonance of the vibration transmitting arm.

2. A power-driven toothbrush according to claim 1 wherein the means for supplying AC current to said solenoid includes a printed circuit board.

3. A power-driven toothbrush according to claim 2 wherein the frequency of the AC current delivered to the solenoid and the natural frequency of the vibration transmitting arm are in the range of 100–300 Hz.

4. A power-driven toothbrush according to claim 2 wherein the means for supplying AC current include an internal or external power supply providing AC current.

5. A power-driven toothbrush according to claim 2 wherein the means for supplying AC current include an internal or external power supply providing DC current which is converted to AC current by the printed circuit board.

* * * * *